United States Patent [19]

Irnich

[11] Patent Number: 4,741,334
[45] Date of Patent: May 3, 1988

[54] MONITORING ARRANGEMENT FOR A HIGH FREQUENCY SURGERY DEVICE

[76] Inventor: Werner Irnich, Birkenweg 60, 6301 Wettenberg 3, Fed. Rep. of Germany

[21] Appl. No.: 860,657

[22] Filed: May 7, 1986

[30] Foreign Application Priority Data

May 7, 1985 [DE] Fed. Rep. of Germany ....... 3516354

[51] Int. Cl.$^4$ ............................................ A61B 17/39
[52] U.S. Cl. ................. 128/303.13; 128/908
[58] Field of Search ............ 128/303.13, 303.14, 128/303.17, 908

[56] References Cited

U.S. PATENT DOCUMENTS 4,122,854 10/1978 Blackett .................. 128/303.13
4,200,105 4/1980 Gonser ..................... 128/303.14

FOREIGN PATENT DOCUMENTS 3306402 9/1984 Fed. Rep. of Germany .
2146534 4/1985 United Kingdom .......... 128/303.13

Primary Examiner—Lee S. Cohen
Attorney, Agent, or Firm—Marmorek, Guttman & Rubenstein

[57] ABSTRACT

A monitoring arrangement is disclosed for a high frequency surgery device, having a control electrode applied on a patient's body, which detects the high frequency voltage existing on the body surface during the treatment and introduces the same to a monitor circuit. The monitor circuit includes a voltage comparator which compares the body surface voltage with a reference voltage $U_{ref}$ and upon exceeding the reference voltage $U_{ref}$, closes a relay which switches off the high frequency surgery device. The reference voltage $U_{ref}$ is determined individually for each patient beforehand and corresponds to the maximum tolerable body surface voltage of the particular patient.

10 Claims, 3 Drawing Sheets

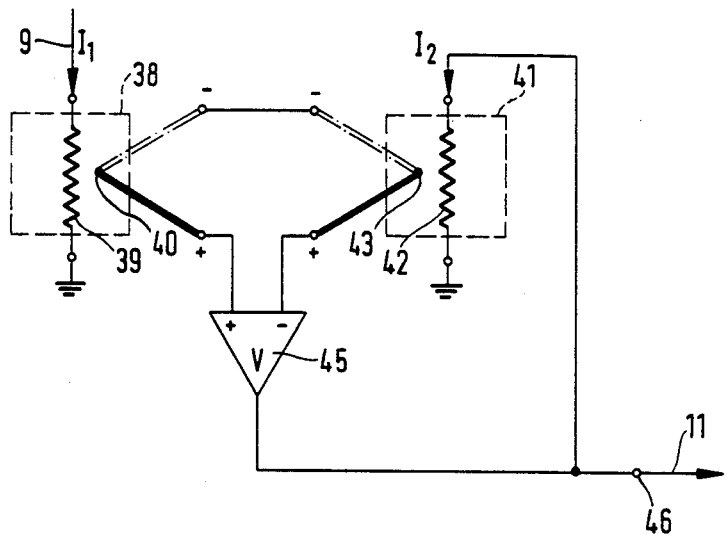
_Fig. 3_
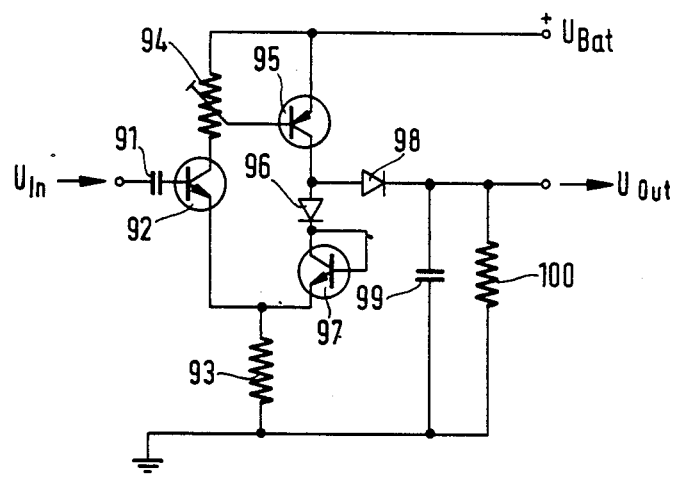
_Fig. 5_

MONITORING ARRANGEMENT FOR A HIGH FREQUENCY SURGERY DEVICE

BACKGROUND OF THE INVENTION

The invention concerns a monitoring arrangement for a high-frequency surgery device. The monitoring arrangement has a control electrode applied on a body, far removed from an active electrode, the control electrode reading during treatment, a high-frequency voltage existing on the body surface relative to the potential of a neutral electrode. The monitoring arrangement also has a monitoring circuit including a voltage comparator controlled by the control electrode. The voltage comparator compares a voltage depending on body surface voltage with a pre-established reference voltage and, upon exceeding the reference voltage, activates a signal transmitter and/or a relay switching-off the high-frequency surgery device.

With a known monitoring apparatus of this type (German patent DE-PS No. 33 06 402), the voltage read by the control electrode is introduced initially to a squaring stage, after which the squared voltage is introduced to an integrating stage, and the squared and integrated voltage is compared in a comparator circuit with a reference voltage. However, this known monitoring arrangement is based upon the premise that the total electrical energy, which is obtained on the one hand from the product of the electrical field strength and the current density, and, on the other hand, from the period of operation, represents a measure for the danger of burning.

It has been shown that even with the same amount of introduced total electrical energy, and even with regular and orderly contact of the neutral electrode to the body surface, the effective heat development at the most loaded body location beneath the neutral electrode is different for individual patients.

The invention is therefore based upon the object of providing a monitoring arrangement for a high-frequency surgery device of the above-described type which, in spite of individual differences in heat development for particular patients, eliminates with certainty any danger of burning.

SUMMARY OF THE INVENTION

This object is attained according to the present invention by introducing to the voltage comparator, on the one hand, a voltage directly proportional to the voltage read by the control electrode and, on the other hand, as reference voltage, a voltage corresponding to a maximum tolerable body surface voltage determined beforehand individually for each patient.

The observed individual differences in heat development in particular patients is readily explained. One factor is that the electrical conductivity of the skin differs as a result of differences in thickness and different moisture of the skin. Another factor is that the capacity of the blood circulation to carry away the electrically-produced heat differs for each individual. Based upon this knowledge it is suggested according to the present invention to employ as criterion for the danger of burning the body surface voltage read off by the control electrode per se, or a voltage directly proportional thereto, which is then compared with the maximum tolerable body surface voltage which has been determined individually for each patient beforehand.

The maximum tolerable body surface voltage for each individual patient, and thereby the reference voltage for the voltage comparator, can be determined in various manners, for example with the aid of the high-frequency surgery device and the control electrode themselves, by means of a single measurement before the operation. For this purpose, the neutral electrode and the control electrode are put on and the high-frequency voltage is introduced across a further large-surface electrode and slowly increased, until the patient subjectively feels a clear sensation of warmth beneath the neutral electrode.

Expediently, however, the individual determination of the maximum tolerable body surface voltage in each individual case follows with the aid of a separate arrangement which includes two contact electrodes arranged at a fixed distance from each other and a high-frequency generator supplying an adjustable high-frequency voltage. In this manner, a determination of the maximum surface voltage and therewith the reference voltage to be adjusted in each individual case, can be performed more easily and quickly. In this case, too, the subjective sensation of pain of the patient can serve as criterion for the maximum surface voltage. Instead, however, an objective temperature measurement can also be advantageously employed, in that, for example, a temperature detecting element is disposed in one or both contact electrodes, which measures the skin temperature. With this embodiment, a temperature between about 43° to 44° C. serves as the indicative value for the maximum tolerable temperature of the skin. In the event that a separate measuring arrangement is employed with two small-surface contact electrodes, with which the contact surface of the electrodes amounts in each case to between about 1 and 2 cm.$^2$, and the electrodes are not removed too far from each other, one then assumes that the voltage between both contact electrodes upon maximum tolerable voltage is approximately twice as high as the maximum tolerable body surface voltage during employment of the high-frequency surgery device.

According to a further embodiment, the monitor arrangement according to the present invention includes a further voltage comparator. A voltage directly proportional to the voltage read by the control electrode is introduced to this additional voltage comparator, along with as reference voltage, a voltage directly proportional to the operational voltage. The ratio of the voltages is so selected that the voltage comparator provides a signal when the body surface voltage exceeds a value of about 10% of the operational voltage. In this manner, one can additionally check whether the neutral electrode is properly in place and a good, large-surface contact to the body surface exists.

This last-mentioned measure proceeds from a consideration that under the prerequisite whereby with proper contact of the neutral electrode, the current flowing through the active electrode and the current flowing through the neutral electrode are identical: Thus, the body surface voltage divided by the transition impedance of the neutral electrode is equal to the total voltage divided by the total impedance of the circuit. By means of conversion, one can derive from this relationship that the ratio of the body-surface voltage to the total voltage is equal to the ratio of the impedance of the neutral electrode to the total impedance. With proper and regular contact of the neutral electrode, this ratio should not, however, be greater than about 1:10. As a result, by means of an examination of the body surface voltage with a viewpoint of noting whether it exceeds about 1/10 of the applied voltage, an unacceptable increase in the transition impedance at the neutral electrode can be determined.

The impedance ratio is, on the other hand, in each case greater than about 3:100. This fact can be utilized according to a further embodiment of the invention, in that, with the aid of a further comparator one can monitor whether the control electrode itself has good contact to the body surface or whether it has become detached under the prevailing circumstances. There are thus, introduced to the further voltage comparator, for this purpose, on the one hand the body surface voltage read from the control electrode and, on the other hand, a voltage directly proportional to the operational voltage, with the ratio of the voltages being so selected that the voltage comparator provides a signal when the voltage read from the control electrode is less than about 3% of the operational voltage.

Finally, the monitor arrangement according to the present invention can be supplemented by means of a further voltage comparator to which one introduces as reference voltage a determined, constant voltage. This further voltage comparator provides a signal when the surface voltage read by the control electrode reaches or exceeds voltage peaks of about 150 V. With the aid of such a monitoring of the voltage peaks, one can now avoid any such burning or even so-called spark discharges through the skin which can occur on account of voltage peaks upon even only short-term impairment of the contact with the neutral electrode. Since in this case the danger of burning is particularly great, the electrosurgery device must to such an extent be switched off by means of the signal given by the voltage comparator.

Further characteristics and advantages of the invention are seen from the following description of specific embodiments along with the drawings.

BRIEF DESCRIPTION OF THE DRAWINGS

FIG. 3 is a circuit diagram showing the construction of a voltage converter employed in the monitor arrangement according to the present invention.

FIG. 5 is a circuit diagram of a peak-value detector that can be employed in the monitor arrangement according to the present invention.

DESCRIPTION OF THE PREFERRED EMBODIMENTS

Figure 1:
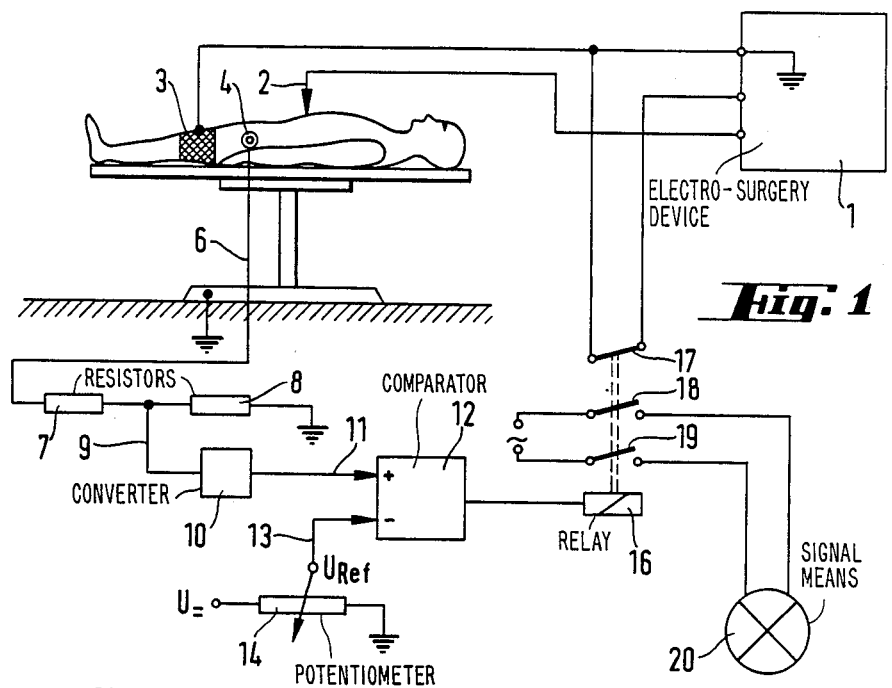
FIG. 1 is a block circuit diagram of the construction of a monitor arrangement according to the present invention.

As is evident from FIG. 1, the active electrode 2 and the neutral electrode 3 are connected to the electrosurgery device 1. The neutral electrode 3 is formed with a large surface and, placed for example on the thigh of the patient, is assumed to have ground potential.

With the aid of the control electrode 4 disposed on the body surface of the patient, which electrode can touch neither the neutral electrode 3 nor any other grounded part, the bodysurface voltage existing relative to the ground potential is read. This voltage existing on the body surface is extensively independent of choice of placement points for the various electrodes, so that the location of the control electrode 4 on the body surface is not critical.

The body-surface voltage read from the control electrode 4 is introduced across conductor 6 to a voltage divider composed of resistances 7 and 8. The body voltage is divided down to achieve a voltage of suitable magnitude for further processing.

This divided high frequency voltage is introduced across conductor 9 to a converter 10, in which the high frequency voltage is converted into a DC voltage corresponding to the RMS value of the high frequency voltage. This DC voltage is introduced across conductor 11 to the positive input of a comparator 12. The negative input of this comparator 12 is connected across conductor 13 to a reference voltage $U_{ref}$, and the comparator 12 compares the voltage introduced across conductor 11 with this reference voltage $U_{ref}$. The reference voltage $U_{ref}$ is obtained with the aid of a potentiometer 14, which is fed by a constant DC voltage $U_=$. This reference voltage $U_{ref}$ is individually adjusted for each patient, after an initial determination is made, for example, with the arrangement described by way of FIG. 2, as to how high to select the reference voltage $U_{ref}$ for the particular patient.

When the voltage introduced from converter 10 to the comparator 12 is greater than or equal to the reference voltage $U_{ref}$, a relay 16 is activated by comparator 12. This relay 16 cuts off the high frequency surgery device 1 across the contact 17 and simultaneously switches on a signal means 20 across the contacts 18 and 19. The signal means 20 provides an optical signal and/or acoustical signal.

Figure 2:
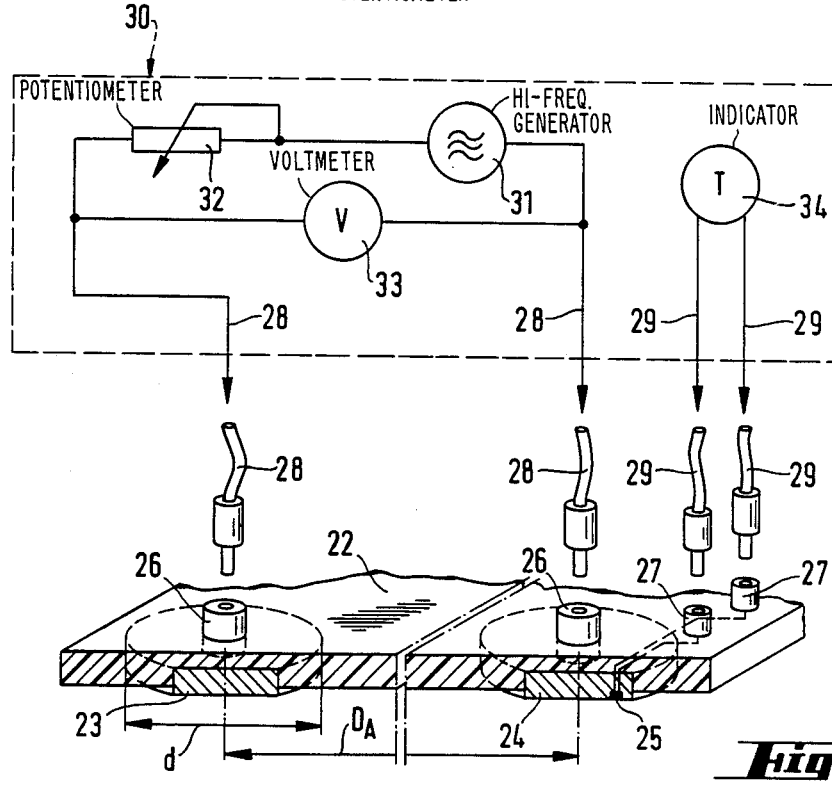
FIG. 2 is a combined circuit diagram and schematic representation of a separate arrangement for individual determination of the maximum tolerable body surface voltage of a patient.

A measuring arrangement such as is described by way of FIG. 2 expediently serves for determination of the magnitude of the reference voltage $U_{ref}$ to be adjusted with potentiometer 14.

As seen in FIG. 2, this measuring arrangement is composed of a carrier plate 22 of an electrically-insulating material in which two e.g., circular-cross-section contact electrodes 23 and 24 are so disposed that by placing the carrier plate 22 on a body part of the patient, they are brought into contact with the skin of the patient. The contact surface of electrodes 23 and 24 amounts to an order of magnitude in each case of approximately 1 to 2 cm$^2$, that is their diameter d amounts always to about 1 to 1.6 cm. The distance $D_A$ between electrodes 23 and 24 amounts to about 10 times their diameter d, i.e, about 10 to 16 cm. In one of electrodes 23 and 24, or, if necessary, in both of these electrodes, a temperature detecting element 25 is integrated, which allows one to measure the temperature of the skin surface.

The carrier plate 22 is provided on the surface lying opposite to the contact side with sockets 26 for the contact electrodes 23 and 24, and with sockets 27 for the thermalelement 25. By means of these sockets 26 and 27, an electrical connection to circuit 30 is effected. This circuit 30, the construction of which is schematically represented, comprises on the one hand a high frequency generator 31, a potentiometer 32 and a voltmeter 33 for provision and control of an adjustable HF-current and, on the other hand, an indicator instrument 34. The HF-voltage is introduced across conductors 28 to both electrodes 23 and 24, and the indicator instrument 34 is connected across conductors 29 to the sockets 27. The measuring instrument 34 serves for indication of the skin temperature. By means of the potentiometer 32, the HF-voltage can be varied to the necessary extent so that with a contact surface of an electrode of about 1 cm$^2$, a current between about 5 and 20 mA flows through the line.

For determination of the reference voltage $U_{ref}$, the carrier plate 22 is thus brought into contact at a suitable place with the skin of the patient, and the electrical connections are made to the circuit 30. Then, with the aid of the potentiometer 32, the HF-voltage between both electrodes is slowly increased, until the patient experiences a still tolerable heating beneath the electrodes. The maximum tolerable heating is provided as a rule when the thermal-element 25 detects a skin surface temperature of about 43°–44° C. When thus the measuring instrument 34 indicates this temperature, the RMS value of this HF-voltage is read off from volt meter 33. The voltage that is read represents the doubled value of the maximum tolerable voltage with the arrangement according to FIG. 1, since with the described measuring arrangement, the voltage is introduced across two electrodes. In order to obtain the reference voltage $U_{ref}$ which is adjusted at potentiometer 14, the RMS value of HF-voltage read from voltmeter 33 must thus be halved.

FIG. 3 schematically represents an example for the construction of a converter 10 with which the high frequency voltage read with control electrode 4 in the monitor circuit described by way of FIG. 1 is converted into a corresponding direct voltage that can be compared as such with the determined reference voltage $U_{ref}$. The represented converter involves a so-called linearizing thermal-converter, known per se. A thermal-converter as is employed for measurement of HF-currents, is composed in known manner of a heating wire, which is heated by means of the current to be measured, and a thermal-element heated by this heating wire, the thermal-electric voltage of which thermal-element serves as a measure for the magnitude of the HF-current. In the "linearizing thermal-converter" of FIG. 3, a thermal-converter 38 which comprises a heating wire 39 and a thermal-element 40, is connected with a similar thermal-converter 41 comprising a heating wire 42 and a thermal-element 43, in a subtraction circuit, whereby the negative poles of both thermal-converters are connected directly with each other and the positive poles of both thermal-transformers lead to an operational amplifier 45. Thus, the positive pole of thermal-element 40 is connected with the positive input of operational amplifier 45, and the positive pole of thermal-element 43 is connected with the negative input of operational amplifier 45. When heat is produced as a means of current $I_1$ in heating wire 39, to which is introduced across conductor 9 the appropriately divided down body surface voltage, there is then provided at the positive input of the amplifier 45 a voltage which appears with amplification V of the amplifier 45 at the output thereof. This output voltage, which can be read at point 46, gives rise to a current flow $I_2$ through the resistance 42 of the thermal-converter 41, and therewith a corresponding heating of this resistance 42, which for its part leads to a voltage at thermal-element 43. The circuit therefore provides that the same heat is always produced at resistances 39 and 42, and that therewith the output voltage furnished by the amplifier 45, which is introduced to the comparator across conductor 11, is always the same as the RMS value of the HF-voltage introduced across conductor 9.

Figure 4:
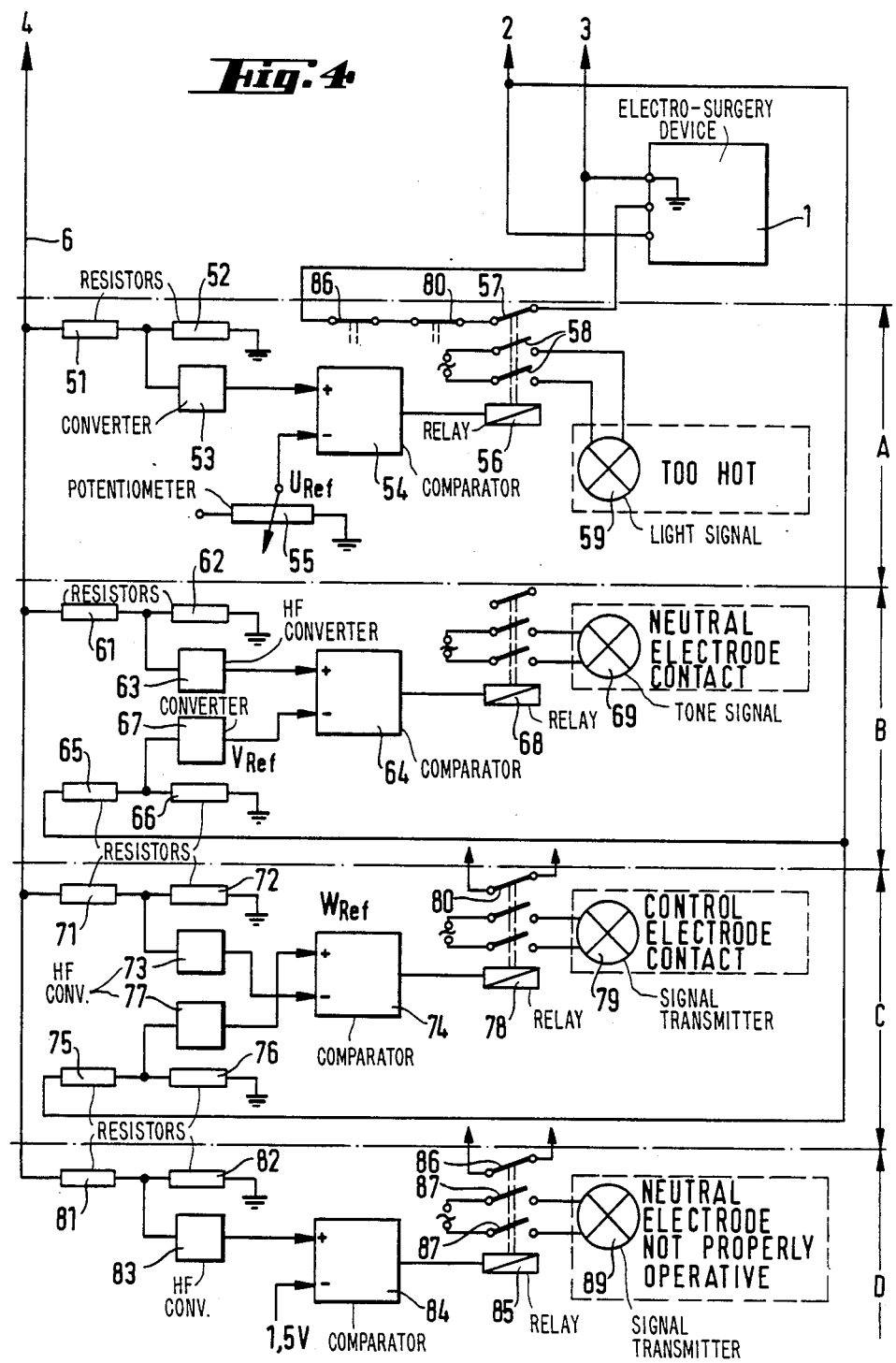
FIG. 4 shows the construction of a monitor arrangement according to the present invention with additional control functions in the form of a block circuit diagram.

FIG. 4 represents the circuit construction of a monitor arrangement which not only provides for avoidance of the danger of an impermissibly high heating, but which, constructed in other respects to the same measuring principle, allows for recognition of even other dangers and defects. The monitor arrangement is controlled by the control electrode 4 across conductor 6 and acts directly on the electro-surgery device, to which lead the neutral electrode 3 and the active electrode 2. The represented circuit is composed of four parts, namely, Part A, Part B, Part C and Part D.

Part A corresponds to the arrangement represented in FIG. 1, and serves for control of the heating of the skin. The HF-voltage read from the body surface is initially divided down to the tenth part in voltage divider 51, 52, and then introduced to a linearizing thermal-converter 53. The direct voltage arising at the output of thermal-converter 53 is compared in comparator 54 with a reference voltage $U_{ref}$, which is determined beforehand for the patients individually and has been correspondingly adjusted in the potentiometer 55. Insofar as the body surface voltage exceeds the reference voltage $U_{ref}$, relay 56 is activated by the comparator 54. The relay 56 expeditiously is formed so that it provides an operational lag of about 1 sec. and self-holding, which operates over a time period of 30–60 seconds. In this case, the electro-surgery device 1 is disconnected across switch contact 57 only for the time period of 30–60 seconds, during which a cooling down of the heated skin region takes place. Thereafter, the relay 56 enables the electro-surgery device 1 again for a time period of 1 second, so that can be further operated as it were intermittently, and a danger of burning is excluded. An occurring instance of danger of overheating of the skin is made recognizable over contact 58 of relay 56 by means of a light signal 59.

Part B of the monitor circuit serves for testing the neutral electrode 3, i.e., whether or not it is in good contact with the body surface of the patient. The body surface voltage read from control electrode 4 and arriving across conductor 6 is divided down again in voltage divider 61, 62, to the tenth part and introduced to a HF-converter 63. The HF-converter involves in this case a peak-value detector, the output DC voltage of which corresponds to the peak-value of the introduced HF-voltage. The output DC voltage of converter 63 is introduced to comparator 64.

Introduced as reference voltage to comparator 64 is a voltage $V_{ref}$ which is derived from the operational voltage of surgery device 1. For this purpose, the operational voltage read at the lead to active electrode 2 is divided down in a voltage divider with resistances 65 and 66 to the hundredth part. This so-reduced voltage is introduced to a converter 67, which can involve a linearizing thermal-converter which provides an output DC voltage corresponding to the RMS value of the HF-input voltage. This output DC voltage serves as reference voltage $V_{ref}$ for the comparator 64. The comparator 64 produces at its outlet signal when the entering voltages reach a ratio of 1:10, that is when a hundredth of the operational voltage is less than or equal to a tenth of the body surface voltage. In this case, the relay 68 is activated by the comparator 64, which thereupon is activated and, across its contact, produces a light or tone signal 69 as indication that the contact of the neutral electrode has worsened.

Part C of the monitor circuit examines whether the control electrode 4 maintains an unobjectionable contact to the body surface of the patient. The body surface voltage is divider down in this case, with the aid of the voltage divider composed of both resistances 71 and 72, to a third, and is introduced across HF-converter 73, which can involve a peakvalue detector such as the one described below in connection with FIG. 5, to the negative input of comparator 74. A voltage derived from the operational voltage of the electro-surgery device 1 is employed again as reference voltage $W_{ref}$. The operational voltage read from the lead to active electrode 2 is for this purpose divided down in the voltage divider composed of resistances 75 and 76, to the hundredth part and the introduced as reference voltage $W_{ref}$ across the HFconverter 77, which can again involve a peak-value detector corresponding to that described in FIG. 5, to the positive input of comparator 74.

With the described layout of the circuit of Part C, the comparator 74 carries a high potential at its output as soon as the body surface voltage amounts to less than 3% of the output voltage of the HF-surgery device. The comparator 74 activates relay 78, which switches off the electro-surgery device 1 across contact 80. Simultaneously, relay 78 switches on the signal transmitter 79 across its contacts. The signal transmitter 79 indicates optically and/or acoustically that the control electrode 4 is no longer properly seated and therefore an examination is necessary.

Part D of the monitor circuit makes it possible, finally, to recognize and automatically exclude the dangers which occur upon faulty neutral electrodes or upon unsatisfactory contact of the neutral electrode. Namely, when the neutral electrode 3 has no or unsatisfactory contact with the body surface does the danger exist that high voltage peaks will arise on the body surface, which can lead to spark-overs between the body and the neutral electrode and, as a result of these, to corresponding injuries.

As with the previously described parts of the monitor circuit, also with Part D is the body surface voltage read from control electrode 4, divided down to the hundredth part with the aid of a voltage divider composed of both resistances 81 and 82. The so-reduced voltage again is introduced into a HF-converter 83, which in this case is formed as a peakvalue detector, such as the one described by way of FIG. 5. The DC voltage furnished from HF-converter 83 is led to the positive input of comparator 84. Serving as reference voltage in this case is a constant DC voltage of 1.5 V. In this manner, the relay 85 is activated by comparator 84 as soon as the body surface voltage reaches or exceeds a value of 150 V. Relay 85 switches off the electro-surgery device across its contact 86. The likewise operated contact 87 of relay 85 switches on an optical and/or acoustical signal transmitter 89, by means of which it is indicated that the neutral electrode is not, or is not properly, positioned.

The construction of a peak-value detector suitable for employment in the monitor circuit as a HF-converter, for example in the case of HF-converters 73, 77 and 83, is described with greater particularity by way of FIG. 5.

The HF-voltage $U_{in}$ is introduced to transistor 92 across coupling capacitor 91. When the voltage $U_{in}$ is greater than 0.5 V, the transistor 92 operates as an emitter follower to the emitter resistance 93. The collector current of transistor 92 produces in potentiometer 94 a voltage drop, with which the base current of transistor 95, and therewith also its collector current, can be regulated. A part of the collector current of transistor 95 flows through diode 96 and transistor 97 which acts as a steepened diode. The diode 96 and transistor 97 have the object of stepping up the potential of two diode drops with respect to the potential of emitter resistance 93. The other part of the collector current from transistor 95 flows across diode 98 and charges the capacitor 99. Since the charging operation across transistor 95 and diode 98 takes place very quickly, and the discharging operation across resistance 100 proceeds, however, slowly, after a few positive half-waves, the entering HF-voltage $U_{in}$ has charged capacitor 99 to an output voltage $U_{out}$ which corresponds to the peak-value of the input voltage $U_{in}$. With the aid of potentiometer 94, the peak-value detector can be so adjusted that a peak value of the entering voltage $U_{in}$ of 1V corresponds to an output voltage $U_{out}$ of likewise 1 V. The time constant of capacitor 99 and resistance 100 is so selected that the output voltage $U_{out}$ lasts long enough so that it can be compared with the reference voltage in the subsequent voltage comparator. When the voltage comparator operates, for example, in the 0.1 ms range, then a time constant of, for example, 2 ms is sufficient for the combination of capacitor 99 and resistance 100.

The monitor circuit according to the present invention is described in connection with embodiments in which analog signals are processed in the voltage comparators. It is obviously also possible to employ digital techniques and the application of a microprocessor for processing above mentioned signals. Finally, the above described embodiments of the invention are intended to be illustrative only. Numerous alternative embodiments may be devised by those skilled in the art without departing from the spirit and scope of the foregoing claims.

I claim:
1. A high frequency surgical apparatus comprising:
   a neutral electrode adapted to be affixed to a patient's body,
   monitoring means operable for determining sufficiency of the contact of said neutral electrode,
   an active electrode adapted for treatment of the patient's body,
   a high frequency current generator coupled to said active and neutral electrodes,
   a control circuit, said control circuit comprising
      a control electrode adapted to be affixed to the patient's body at a distance from said active electrode for detecting a high frequency body surface voltage relative to said neutral electrode,
      conversion means for converting said high frequency body surface voltage detected by said control electrode into a. directly proportional D.C. voltage,
      a first voltage comparator having first and second inputs, said first input being coupled to said conversion means to receive said D.C. voltage corresponding to said high frequency body surface voltage, said second input being coupled to receive a first reference voltage determined individually for the patient and corresponding to approximately the maximum individually tolerable body surface voltage for the patient, and
   switch means actuated by said first voltage comparator for turning off said high frequency current generator when said D.C. voltage corresponding to said high frequency body surface voltage exceeds said reference voltage, and said monitoring means comprising a second voltage comparator having, first and second inputs, the first input of said second voltage comparator being coupled to said conversion means to receive a first voltage relating to said D.C. voltage and the second input of said second voltage comparator being coupled to receive a predetermined second voltage, said second voltage comparator providing an output signal when said first voltage exceeds a predetermined fraction of said second voltage.

2. The apparatus of claim 1, further comprising a signal means coupled to said switch means and operable for providing a voltage when said D.C. voltage exceeds said reference signal.

3. The apparatus of claim 2, wherein said signal produced by said signal means is a light.

4. The apparatus of claim 2, wherein said signal produced by said signal means is a tone.

5. A high frequency surgical apparatus comprising
a neutral electrode adapted to be affixed to a patient's body,
an active electrode adapted for treatment of the patient's body,
a high frequency current generator coupled to said active and neutral electrodes,
a control circuit, said control circuit comprising
a control electrode adapted to be affixed to the patient's body at a distance from said active electrode for detecting a high frequency body surface voltage relative to said neutral electrode,
monitoring means operable for determining the sufficiency of the contact of said neutral electrode,
conversion means for converting said high frequency body surface voltage detected by said control electrode into a directly proportional D.C. voltage,
a first voltage comparator having first and second inputs, said first input being coupled to said conversion means to receive said D.C. voltage corresponding to said high frequency body surface voltage, said second input being coupled to receive a reference voltage determined individually for the patient and corresponding to approximately the maximum individually tolerable body surface voltage for the patient, and
switch means actuated by said voltage comparator for turning off said high frequency current generator when said D.C. voltage corresponding to said high frequency body surface voltage exceeds said reference voltage, and
said monitoring means comprising a second voltage comparator having first and second inputs, the first input of said second voltage comparator being coupled to said conversion means to receive a first voltage relating to said D.C. voltage and the second input of said second voltage comparator being coupled to receive a predetermined second voltage, said second voltage comparator providing an output signal when said first voltage exceeds a predetermined fraction of said second voltage.

6. The apparatus of claim 5, further comprising a signal means coupled to said switch means and operable for providing a voltage when said D.C. voltage exceeds said reference signal.

7. The apparatus of claim 6, wherein said signal produced by said signal means is a light.

8. The apparatus of claim 6, wherein said signal produced by said signal means is a tone.

9. A high frequency surgical apparatus comprising
a neutral electrode adapted to be affixed to a patient's body,
an active electrode adapted for treatment of the patient's body,
a high frequency current generator coupled to said active and neutral electrodes, and
a control circuit, said control circuit comprising
a control electrode adapted to be affixed to the patient's body at a distance from said active electrode for detecting a high frequency body surface voltage relative to said neutral electrode,
conversion means for converting said high frequency body surface voltage detected by said control electrode into a directly proportional D.C. voltage,
a voltage comparator having first and second inputs, said first input being coupled to said conversion means to receive said D.C. voltage corresponding to said high frequency body surface voltage, said second input being coupled to receive a reference voltage determined individually for the patient and corresponding to approximately the maximum individually tolerable body surface voltage for the patient, and
switch means actuated by said voltage comparator for turning off said high frequency current generator when said D.C. voltage corresponding to said high frequency body surface voltage exceeds said reference voltage.

10. A method of high frequency surgery comprising
connecting a neutral electrode to a patient's body,
connecting an active electrode to the patient's body,
generating a high frequency current between said active and neutral electrodes,
connecting a control electrode to the patient's body at a distance from said active electrode for detecting a high frequency body surface voltage relative to said neutra electrode,
converting said high frequency body surface voltage detected by said control electrode into a directly proportional D.C. voltage,
comparing said D.C. voltage to a reference voltage determined individually for the patient and corresponding to approximately the maximum individually tolerable body surface voltage for the patient, and
turning off said high frequency current generator when said D.C. voltage exceeds said reference voltage.

* * * * *